United States Patent [19]

Ramakers

[11] Patent Number: 5,147,633
[45] Date of Patent: Sep. 15, 1992

[54] ALKYL SULPHATE SALTS

[75] Inventor: Hubert-Pierre-Eugene Ramakers, Angleur, Belgium

[73] Assignee: ICI Renory SA/NV, Seraing, Belgium

[21] Appl. No.: 620,940

[22] Filed: Dec. 3, 1990

[30] Foreign Application Priority Data

Dec. 1, 1989 [GB] United Kingdom ............ 8927213

[51] Int. Cl.$^5$ ................................. A61K 7/16
[52] U.S. Cl. ........................... 424/56; 424/49; 514/772
[58] Field of Search ..................... 424/49-58

[56] References Cited

U.S. PATENT DOCUMENTS

| | | | |
|---|---|---|---|
| 3,521,370 | 7/1970 | Senatore et al. | 34/9 |
| 3,607,763 | 9/1971 | Salmen et al. | 252/526 |
| 4,238,476 | 12/1980 | Harley | 424/52 |
| 4,419,342 | 12/1983 | Hayes et al. | 424/54 |

FOREIGN PATENT DOCUMENTS

| | | |
|---|---|---|
| 129276 | 12/1984 | European Pat. Off. . |
| 179533 | 4/1986 | European Pat. Off. . |
| 2134215 | 1/1972 | Fed. Rep. of Germany . |
| 2335619 | 2/1974 | Fed. Rep. of Germany . |
| 2553141 | 6/1976 | Fed. Rep. of Germany . |
| 1280350 | 11/1961 | France . |
| 800483 | 4/1955 | United Kingdom . |
| 2106483 | 4/1983 | United Kingdom . |

*Primary Examiner*—Shep K. Rose
*Attorney, Agent, or Firm*—Cushman, Darby & Cushman

[57] ABSTRACT $C_{10}$ to $C_{20}$ alkyl sulphate salts of which at least 15% of the alkyl groups are branched and formulated as free flowing particulate compositions which comprise a polyalkylene glycol and/or a glycol diester or glycerol triester of a $C_{12}$ to $C_{24}$ alkanoic acid.

11 Claims, No Drawings

ALKYL SULPHATE SALTS

This invention relates to alkyl sulphate salts.

Salts of sulphates of alkanols having 10 to 20 carbon atoms are used as surfactants. The salts may be for example ammonium, substituted ammonium, for example mono-di- or tri-ethanolamine or alkali metal, for example sodium, potassium or lithium salts or magnesium salts. Such salts tend however to be sticky if a substantial proportion of the alkyl groups is branched. Such stickiness makes them difficult to handle, and if they are spray dried they tend to be difficult to remove from the spray drier and may create blockages.

We have found that such salts may be produced in a free flowing particulate form, for example as flakes or powders if minor proportions of certain additives are incorporated in them.

This invention therefore comprises a free flowing particulate composition which comprises at least 85% and preferably at least 90% by weight of an alkyl sulphate salt of which the alkyl group has 10 to 20, for example 13 to 15 carbon atoms of which at least 15% for example at least 35% or at least 45% and up to 100% but preferably at most 70% of the alkyl groups are branched, and 1 to 10% and preferably 2 to 6% by weight of a polyalkylene glycol which is solid at 20° C. Other materials which may be present include the corresponding unsulphated alcohol, free base and/or sulphate salts, for example substituted ammonium, alkali metal or magnesium sulphates. The polyalkylene glycol may be a copolymer of ethylene glycol and other alkylene glycol residues, for example butylene or preferably propylene glycol residues, but it is more preferably a polyethylene glycol.

If the alkyl sulphate salt is a salt of an alkali metal or magnesium it may be desired to produce compositions according to the invention by spray drying, as such salts are sufficiently heat stable for such treatment. Suitably a solution of the alkyl sulphate salt and the polyalkylene glycol which comprises 35 to 70% by weight of water is spray dried co-currently with a stream of gas with an initial temperature of for example 170° to 240° C. which may fall in the process to about 100° C. for example 80° to 120° C., but preferably from above 100° C. to 120° C. if the gas outlet is at atmospheric pressure. Conventional apparatus may be used; for example droplets may be formed by means of spray jets or a rotating disc.

An important use for the composition of the invention is in the manufacture of toothpaste. The components of the compositions are sufficiently non-toxic for this use and they are readily handled and processed in this application.

EXAMPLE

A solution A in water at 50° C. of the sodium salt of an alkyl sulphate of which the alkyl groups were a mixture of 67% $C_{13}$ and 33% $C_{15}$ groups with substantial chain branching (approx 50% of the alkyl groups being branched) (30% by weight) and containing 1% of free alcohol and 0.8% of sodium sulphate, a buffer comprising ammonium bi-carbonate (0.2%) and sodium bicarbonate (0.1%), was made up. Similar solutions B and C but comprising also 0.75% and 1.5% respectively of polyethylene glycol of average molecular weight 6000 were also prepared. All percentages are by weight.

All three solutions were spray dried in co-current flow with air at an air inlet temperature of 205° C., and an air outlet temperature of 105° C. The solution inlet temperature was 50° C. and a rotating disc distributor operating at 6700 revolutions per minute was used to form droplets.

The products of spray drying had the following composition.

|  | A | B | C |
|---|---|---|---|
| Active Matter MW 312 | 95.2 | 93.2 | 90.8 |
| Sodium Sulphate | 2.5 | 2.4 | 2.4 |
| Unsulphated Matter | 1.7 | 1.6 | 1.5 |
| PEG 6000 | 0 | 2.4 | 4.7 |
| Water | 0.6 | 0.4 | 0.6 |

Product A is sticky, remaining on the wall of the spray drier. Product B and C, are free flowing, but B is slightly sticky.

What is claimed is:

1. A free flowing particulate composition suitable for use as a toothpaste additive which comprises at least 85% by weight of an alkyl sulphate salt of which the alkyl group has 10 to 20 carbon atoms of which at least 15% of the alkyl groups are branched and which has a tendency to stickiness, and 1 to 10% by weight of a polyalkylene glycol which is solid at 20° C. and which functions to avoid the stickiness of said salt.

2. A composition as claimed in claim 1 in which the alkyl group has 13 to 15 carbon atoms.

3. A composition as claimed in claim 1 in which 35 to 70% of the alkyl groups are branched.

4. A composition as claimed in claim 1 which comprises 2 to 6% of polyalkylene glycol.

5. A composition as claimed in claim 1 in which the polyalkylene glycol is polyethylene glycol.

6. A composition as claimed in claim 5 in which the polyalkylene glycol has a molecular weight of 3000 to 10000.

7. A composition as claimed in claim 1 which comprises unsulphated alcohol corresponding to the alkyl sulphate salt, free base and/or other sulphate salts.

8. A composition as claimed in claim 1 in which the alkyl sulphate salt is an alkali metal or magnesium salt.

9. A process of producing a free flowing, spray-dried particulate composition as claimed in claim 1 in which a solution of an alkali metal or magnesium salt of an alkyl sulphate wherein the alkyl group has 10 to 20 carbon atoms of which at least 15% of the alkyl groups are branched and which salt normally has a tendency to stickiness and the polyalkylene glycol, which solution comprises 35 to 70% by weight of water, is spray dried co-currently with a stream of gas.

10. A composition according to claim 1 comprising at least 90% by weight of said salt.

11. A composition according to claim 1 which is a spray-dried, free-flowing particulate toothpaste additive.